United States Patent [19]

Hoeffkes et al.

[11] Patent Number: 4,948,528

[45] Date of Patent: Aug. 14, 1990

[54] FREE-FLOWING PEARLESCENT CONCENTRATE

[75] Inventors: Horst Hoeffkes; Anke Kaczich, both of Duesseldorf, Fed. Rep. of Germany

[73] Assignee: Henkel Kommanditgesellschaft auf Aktien, Duesseldorf, Fed. Rep. of Germany

[21] Appl. No.: 303,373

[22] Filed: Jan. 27, 1989

Related U.S. Application Data

[62] Division of Ser. No. 125,506, Nov. 25, 1987, Pat. No. 4,824,594.

[30] Foreign Application Priority Data

Nov. 28, 1986 [DE] Fed. Rep. of Germany ....... 3640755

[51] Int. Cl.$^5$ ............................................. B01F 17/56
[52] U.S. Cl. ..................................... 252/357; 252/351; 252/DIG. 5; 252/DIG. 13; 252/548; 424/70
[58] Field of Search .................. 424/70; 252/351, 357, 252/DIG. 13, DIG. 5, 548

[56] References Cited

U.S. PATENT DOCUMENTS 4,470,982  9/1984  Winkler ............................ 424/70 X
4,488,981  12/1984  Urfer et al. ........................ 252/548
4,604,282  8/1986  Grollier et al. ........ 252/DIG. 13 X
4,654,163  3/1987  Quack et al. ........... 252/DIG. 13 X
4,663,069  5/1987  Llenado .................. 252/DIG. 13 X

FOREIGN PATENT DOCUMENTS 57-155279  9/1982  Japan ................................... 252/356
61-005005  1/1986  Japan ..................................... 424/70
128627A    5/1984  United Kingdom .................. 424/70

Primary Examiner—Richard D. Lovering
Assistant Examiner—Daniel S. Metzmaier
Attorney, Agent, or Firm—Ernest G. Szoke; Wayne C. Jaeschke; Real J. Grandmaison

[57] ABSTRACT

A pearlescent concentrate in the form of a free-flowing dispersion containing from 5 to 15% by weight of one or more ester corresponding to the following formula $$R^1-(OC_nH_{2n})_x-OR^2$$

and from 1 to 6% by weight of one or more fatty acid mono- ethanolamide may be prepared using from 2 to 8% by weight of one or more compound selected from the group alkyl (oligo) glucoside, sorbitan fatty acid ester, fatty amine ethoxylate, ether carboxylic acid, or fatty acid monoester or diester of glycerol ethoxylate as an emulsifier.

8 Claims, No Drawings

FREE-FLOWING PEARLESCENT CONCENTRATE

This is a division of Application Ser. No. 125,506, filed Nov. 25, 1987, now U.S. Pat. No. 4,824,594.

BACKGROUND OF THE INVENTION

1. Field of the Invention

This invention relates to a pearlescent concentrate in the form of a free-flowing aqueous dispersion.

Aqueous compositions of surfactants and cosmetic preparations can be given a pearlescent, aesthetically attractive appearance by incorporation of substances which, after cooling, precipitate in the form of fine, nacreous crystals and remain dispersed in the compositions. Suitable pearlescers include, for example, the monoesters and diesters of ethylene glycol, propylene glycol and oligomeric alkylene glycols of this type or glycerol with $C_{16}$–$C_{22}$ fatty acids and also monoalkanolamides of $C_{12}$–$C_{22}$ fatty acids with alkanolamines containing 2 or 3 carbon atoms.

It is also known that the pearlescers mentioned above can be stably dispersed in water or in aqueous surfactant solutions and that the concentrated pearlescent dispersions thus obtained may be added without heating to the preparations to be made pearlescent, so that there is no need for the heating and cooling otherwise necessary for incorporation to form the pearlescent crystals.

2. Discussion of Related Art

Pearlescent concentrates based on the pearlescers mentioned above are known, for example, from German patent application 16 69 152 and from Japan patent application 56/71021 (Chem. Abstr. 95/156360). The pearlescent concentrates known from Japan application 56/71021 are attended by the disadvantage that they are not free-flowing and do not form stable, free-flowing dispersions on corresponding dilution with water. This makes the concentrates very difficult to handle and process on an industrial scale. The pearlescent concentrates known from German application 16 69 152 contain anionic surfactants to stabilize the dispersion in its liquid state. These concentrates have the disadvantage that, in formulations containing constituents of opposite ionicity, they are incompatible and impair the stability of the dispersion or, in formulations containing cationic conditioning constituents, lead to a reduction in the conditioning effect. It has been found that many nonionic and zwitterionic emulsifiers lead either to pearlescent dispersions of low stability and brilliance or to pearlescent dispersions which, in cationic hair-care formulations, reduce the effect of the cationic conditioning constituents. Accordingly, an object of the present invention is to provide emulsifiers with which it is possible to prepare free-flowing pearlescent dispersions combining high brilliance and high stability with high compatibility with cationic conditioning components.

DESCRIPTION OF THE INVENTION

Other than in the operating examples, or where otherwise indicated, all numbers expressing quantities of ingredients or reaction conditions used herein are to be understood as modified in all instances by the term "about".

The present invention relates to a pearlescent concentrate in the form of a free-flowing dispersion comprising from 5 to 15% by weight of one or more ester corresponding to the following formula $$R^1\text{---}(OC_nH_{2n})_x\text{---}OR^2 \qquad (I)$$

in which $R^1$ is a linear $C_{16}$–$C_{22}$ fatty acyl group, $R^2$ is hydrogen or an $R^1$ group, n is 2 or 3, and x is a number from 1 to 4; and from 1 to 6% by weight of one or more monoethanolamide of a $C_{12}$–$C_{22}$ fatty acid, wherein the concentrate contains as an emulsifier from 2 to 8% by weight of one or more compound corresponding to general formulae II to VI below, $$H\text{---}(C_6H_{10}O_5)_y\text{---}OR^3 \qquad (II)$$

being an alkyl (oligo) glucoside, in which y is the average degree of oligomerization and is equal to 1 to 5 and $R^3$ is a $C_6$–$C_{12}$ alkyl group,

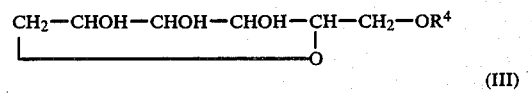

(III)

being a sorbitan monofatty acid ester, in which $R^4$ is a $C_{12}$–$C_{18}$ fatty acyl group,

(IV)

being a fatty amine ethoxylate, in which $R^5$ is a $C_{12}$–$C_{18}$ alkyl group and the sum of p +q is equal to 2 to 12,

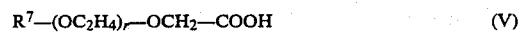

(V)

being an ether carboxylic acid, in which $R^7$ is a $C_{12}$–$C_{16}$ alkyl group and r is equal to 2 to 8, and

(VI)

being a fatty acid monoester or diester of a glycerol ethoxylate, in which $R^4$ is a $C_{12}$–$C_{18}$ fatty acyl group, $R^5$ and $R^6$ are hydrogen or one of the groups $R^5$ and $R^6$ is a group $R^4$ and the other is hydrogen and the sum of s+t+u is equal to 4 to 20.

In addition, the pearlescent concentrates according to the invention contain water in a quantity of from about 70 to 90% by weight, based on the weight of the concentrate. The pearlescent concentrates which may be prepared with the emulsifiers corresponding to formulae 11 to VI above are free-flowing at room temperature (approx. 10 to 20° C) and show a pearlescence which is stable to at least 50° C which even preparations containing the concentrates retain despite variations in temperature. The pearlescent crystals show high brilliance and, even after melting or dissolution by heating beyond the melting point, are reformed on cooling in the same brilliant, uniform crystal form.

Suitable esters corresponding to formula (I) $R^1(OC_nH_{2n})_xOR^2$ include, for example, the monoesters and diesters of ethylene glycol and propylene glycol with higher fatty acids, for example with palmitic acid, stearic acid or behenic acid, or the diesters of diethylene glycol or triethylene glycol with those fatty acids. Also suitable are mixtures of monoesters and diesters of the glycols mentioned with fatty acid mixtures, for example with hardened tallow fatty acid or with the saturated $C_{16}$–$C_{18}$ fatty acid fraction of tallow fatty acid. The ethylene glycol monoester and/or diester of palmitic and/or stearic acid is particularly suitable.

Suitable monoethanolamides of $C_{12}$–$C_{18}$ fatty acids include, for example, lauric acid monoethanolamide, myristic acid monoethanolamide, palmitic/stearic acid monoethanolamide and, above all, the monoethanolamide of the $C_{12}$–$C_{18}$ fraction of coconut oil fatty acid.

Suitable alkyl glucosides of formula 11 include, in particular, the products in which $R^3$ is a $C_8$–$C_{10}$ alkyl group and the degree of oligomerization y is from 1.2 to 2. Products such as these are commercially available, for example, under the trademarks Triton ® BG 10 and Triton ® CG 110 (Rohm and Haas).

Sorbitan fatty acid esters corresponding to formula III are also commercially available, and include for example sorbitan monolaurate (Span ® 20), sorbitan monopalmitate (Span ® 40), sorbitan monostearate (Span ® 60) and sorbitan monooleate (Span ® 80).

Suitable fatty amine ethoxylates of formula IV include, for example, an adduct of 2 moles ethylene oxide with tallow amine (Duomeen ® T/12) or an adduct of 10 moles ethylene oxide with a cocosamine (Duomeen ® C/20).

Suitable ether carboxylic acids of formula V are known from the literature, for example from German patent specification 974 011 or German patent specification 975 850. Products of this type are also commercially available, for example under the tradename "SANDOPAN DTC" (isotridecyloxypoly (7) ethoxyacetic acid).

Fatty acid monoesters and diesters of glycerol ethoxylates corresponding to formula VI are known, for example, from German patent specification 20 24 051. One particularly suitable product of this type is the product described as Example A in said patent specification which is commercially available under the trademark Cetiol ® HE.

The pearlescent concentrates according to the invention show a particularly silky to metallic pearlescence when they contain a combination of from 5 to 8% by weight of an ethylene glycol monostearate and distearate, preferably in a ratio by weight of from 1 : 2 to 1 : 5, and from 2 to 5% by weight of triethylene glycol distearate as the pearlescing ester of formula I.

Instead of ethylene glycol monostearate and distearate and triethylene glycol distearate, it is also possible to use the corresponding esters of palmitic acid/stearic acid mixtures, in which case the mixture should contain at least 50% by weight of stearic acid.

Particularly stable pearlescent concentrates are obtained where from 6 to 10% by weight of the pearlescing ester corresponding to formula I, from 3 to 5% by weight of a $C_{12}$-$C_{18}$ coconut oil fatty acid monoethanolamide, and from 4 to 6% by weight of an emulsifier corresponding to formulae 11 to VI are present therein.

In addition to the compulsory components mentioned, the pearlescent concentrates according to the invention contain water as an essential ingredient. They may also contain a small quantity of preservative, for example formaldehyde, Na benzoate, sorbic acid, p-hydroxybenzoic acid ester, 5-bromo-5-nitro-1, 3-dioxane and other preservatives suitable for aqueous preparations. Small quantities of buffers to adjust the pH value to between 6 and 8, for example citric acid and/or sodium citrate, may also be present.

The pearlescent concentrates according to the invention are prepared by initially heating the pearlescing solids and emulsifiers together beyond their melting point, preferably to a temperature of from 75 to 100° C, accompanied by mixing. The water, likewise heated to between 75 and 100° C, is then added with stirring to the melt thus formed. The water may contain preservatives and buffers. The emulsion formed is then cooled with stirring to about +50° C in 5 to 20 minutes and homogenized briefly, for example for 1 to 3 minutes, at that temperature using a homogenizer or dispersion unit capable of generating intense shear forces. Static and dynamic mixing units, for example slot-type homogenizers or dispersion units operating on the stator-rotor principle, are suitable for this purpose. After this brief and intensive homogenization, the dispersion formed is further cooled with slow stirring to room temperature.

One particularly preferred process for preparing the pearlescent concentrate according to the invention is characterized in that (a) the pearlescing solids, emulsifiers and a first portion of the water heated individually or together and thoroughly mixed to form an emulsion of which the temperature is 1 to 30° C. above the melting or crystallization temperature of the pearlescing solids, after which (b) the second portion of water is added, its temperature being gauged in such a way that the dispersion formed assumes a temperature 3 to 15° C. below the crystallization temperature of the pearlescing solids. This process is particularly suitable for continuous production. The pearlescent concentrates according to the invention are suitable for creating pearlescence in aqueous surfactant preparations of any ionicity and in aqueous cosmetic preparations, irrespective of whether they contain cationic or anionic surfactants or polymers. To create pearlescence, 1 to 20% by weight of the pearlescent concentrate according to the invention is distributed in the aqueous preparation. The pearlescent concentrate may be distributed with gentle stirring without any need for heating, i.e. at a temperature of from 10 to 30° C.

The following Examples are intended to illustrate the invention without limiting it in any way.

EXAMPLE I

Pearlescent concentrates having the following compositions were prepared:

| | |
|---|---|
| ethylene glycol stearate (CTFA name: glycol distearate) | 8.0 kg |
| coconut oil fatty acid ($C_{12}$-$C_{18}$) monoethanolamide | 4.0 kg |
| emulsifier (A–J) | 5.0 kg |
| water | 83.0 kg |

The following compounds were successively used as the emulsifier:

A. Alkyl($C_8$–$C_{10}$)oligo(1,8)-glucoside
  (Triton ® BG 10, Rohm and Haas)
B. Alkyl(CB-C10)oligo-(1,3)-glucoside
  (Triton ® CG 110, Rohm and Haas)
C. Sorbitan monolaurate
  (Span ® 20, Atlas Chemical)
D. Soritan monopalmitate
  (Span ® 40, Atlas Chemical)
E. Sorbitan monostearate
  (Span ® 60, Atlas Chemical)
F. Sorbitan monooleate
  (Span ® 80, Atlas Chemical)

G. Cocosamine ethoxylate (12 moles ethylene oxide) (Araphen ® K 100, Henkel KGaA)

H. Tallow amine ethoxylate (2 moles ethylene oxide) (Ethomeen ® T 12, Armour)

I. $C_{13}H_{27}-(OCH_2-CH_2)_6-O-CH_2-COOH$ (Sandopan ® DTC-Acid, Sandoz)

J. Glycerol ethoxylate (7.4 moles ethylene oxide) fatty acid $C_8-C_{18}$ monoester The concentrates were prepared as follows:

The mixture of ethylene glycol stearate, coconut oil fatty acid monoethanolamide and the emulsifier was heated to 75° C. 8 kg water were then heated to 75° C. and added and an emulsion formed by homogenization using a turbine. The remaining 75 kg of water were then heated to 25° C. and added to the emulsion with stirring. A dispersion having a temperature of 47° C. was formed, assuming a pearlescent appearance after a few minutes. The dispersion was then poured into a storage vessel and was then suitable for further use.

EXAMPLE II

Pearlescent concentrates A to J were used in the following formulations:

Pearlescent Hair Rinse

An emulsion-form hair rinse comprising;

| | |
|---|---|
| 3% by weight cetyl/stearyl alcohol, | 8 kg |
| 0.5% by weight cetyl trimethylammonium chloride, | |
| 96.5% by weight water, | |
| Pearlescent concentrate A to J | 2 kg |

Hair rinses having an attractive pearlescence and a good conditioning effect were obtained.

Pearlescent Hair Shampoo

| | |
|---|---|
| Fatty alcohol ($C_{12}$–$C_{14}$)poly(2EO) glycol ether sulfate, Na salt (28% by weight aqueous solution), | 40 kg |
| N-cocos($C_{12}$–$C_{18}$) acylamidopropyl dimethyl glycine (30% aqueous solution), | 10 kg |
| Pearlescent concentrate A to J, and | 5 kg |
| Water | 45 kg |

Pearlescent shampoos were obtained.

We claim:

1. A pearlescent concentrate in the form of a free-flowing dispersion at room temperature consisting essentially of from about 5 to about 15% by weight of one or more pearlescing ester corresponding to the formula $$R^1-(OC_nH_{2n})_x-OR^2 \quad (I)$$

in which $R^1$ is a linear $C_{16}$-$C_{22}$ fatty acyl group, $R^2$ is hydrogen or an $R^1$ group, n is 2 or 3, and x is a number from 1 to 4; and about 1 to about 6% by weight of one or more monoethanolamide of a $C_{12}$-$C_{22}$ fatty acid; wherein the concentrate contains as an emulsifier from about 2 to about 8% by weight of one or more compound corresponding to general formula II below, $$H-(C_6H_{10}O_5)_y-OR^3 \quad (II)$$

being an alyl (oligo)glucoside, in which y is the average degree of oligomerization and is equal to 1 to 5 and $R^3$ is a $C_6$-$C_{12}$ alkyl group, and from about 70 to about 90% by weight of water, all weights being based on the weight of said concentrate.

2. A pearlescent concentrate as in claim 1 comprising from about 6 to about 10% by weight of said ester corresponding to formula (I), from about 3 to about 5% by weight of a $C_{12}$-$C_{18}$ coconut oil fatty acid monoethanolamide, and from about 4 to about 6% by weight of an emulsifier corresponding to said formula II.

3. A pearlescent concentrate as in claim 1 wherein said ester corresponding to formula (I) is a monoester or diester of ethylene glycol or propylene glycol with a $C_{16}$-$C_{22}$ fatty acid.

4. A pearlescent concentrate as in claim 3 wherein said fatty acid is palmitic acid, stearic acid, or behenic acid.

5. A pearlescent concentrate as in claim 1 wherein said ester corresponding to formula (I) is a diester or diethylene glycol or triethylene glycol with a $C_{16}$-$C_{22}$ fatty acid.

6. A pearlescent concentrate as in claim 1 wherein said monoethanolamide is lauric acid monoethanolamide, myristic acid monoethanolamide, palmitic-stearic monoethanolamide, or coconut oil monoethanolamide.

7. A pearlescent concentrate as in claim 1 wherein $R^3$ in said alkylglucoside of formula (II) is a $C_8$-$C_{10}$ alkyl group, and y is from about 1.2 to about 2.

8. A pearlescent concentrate as in claim 1 wherein said ester corresponding to formula (I) comprises from about 5 to about 8% by weight of an ethylene glycol monostearate and distearate in a weight ratio of from about 1:2 to about 1:5, and from about 2 to about 5% by weight of triethylene glycol distearate.

* * * * *

UNITED STATES PATENT AND TRADEMARK OFFICE
CERTIFICATE OF CORRECTION

PATENT NO. : 4,948,528

DATED : August 14, 1990

INVENTOR(S) : Horst Hoeffkes et al.

It is certified that error appears in the above-identified patent and that said Letters Patent is hereby corrected as shown below:

In the Claims, at claim 1, col. 6, line 16 "alyl" should read --alkyl--.

In the Claims, at claim 5, col. 6, line 35 "or" should read --of--.

Signed and Sealed this

Seventh Day of January, 1992

Attest:

HARRY F. MANBECK, JR.

*Attesting Officer*  *Commissioner of Patents and Trademarks*